United States Patent [19]

Boder et al.

[11] Patent Number: 5,254,582

[45] Date of Patent: Oct. 19, 1993

[54] ANTITUMOR COMPOSITIONS AND METHODS

[75] Inventors: George B. Boder, Martinsville; William J. Ehlhardt, Indianapolis; Gerald B. Grindey, Indianapolis; John E. Toth, Indianapolis; John F. Worzalla, Indianapolis; John L. Zimmermann, Greenfield, all of Ind.

[73] Assignee: Eli Lilly and Company, Indianapolis, Ind.

[21] Appl. No.: 831,604

[22] Filed: Feb. 5, 1992

[51] Int. Cl.[5] .................... A01N 43/08; A61K 31/34
[52] U.S. Cl. ....................................... 514/469; 549/467
[58] Field of Search ......................... 514/469; 549/467

[56] References Cited

U.S. PATENT DOCUMENTS

| | | |
|---|---|---|
| 3,083,207 | 3/1963 | Hoehn et al. |
| 3,097,242 | 7/1963 | Hoehn et al. |
| 3,102,115 | 8/1963 | Breuer et al. |
| 3,736,122 | 5/1973 | Tung et al. |
| 3,849,110 | 11/1974 | Soper et al. |
| 4,659,709 | 4/1987 | Harada et al. |
| 4,845,128 | 7/1989 | Harper et al. |
| 5,116,874 | 5/1992 | Poor ................................. 514/469 |
| 5,169,860 | 12/1992 | Mohamadr et al. .............. 549/467 |

FOREIGN PATENT DOCUMENTS

| | | |
|---|---|---|
| 1208561 | 7/1986 | Canada . |
| 107214 | 9/1983 | European Pat. Off. . |
| 166615 | 1/1986 | European Pat. Off. . |
| 222475 | 5/1987 | European Pat. Off. . |
| 291269 | 11/1988 | European Pat. Off. . |

OTHER PUBLICATIONS

W. J. Ehlhardt, *Drug Metabolism and Disposition*, 19:370 (1991).

J. J. Howbert, et al., *Synthetic Communications*, 20:3193 (1990).

W. J. Ehlhardt, *Drug Metabolism and Disposition*, 19:366 (1991).

J. J. Howbert, et al., *Journal of Medicinal Chemistry*, 33:2393 (1990).

G. B. Grindey, et al., *Proceedings of the American Association of Cancer Research*, 27:277 (Abstract 1099) (1986).

C. W. Taylor, et al., *Journal of Clinical Oncology*, 7:1733 (1989).

J. D. Hainsworth, et al., *Cancer Research*, 49:5217 (1989).

R. Levine, *Diabetes Care*, 7 (Suppl. 1):3-7 (1984).

G. F. Holland, et al., *Journal of Medicinal and Pharmaceutical Chemistry*, 3:99 (1961).

P. J. Houghton, et al., *Cancer Chemotherapy and Pharmacology*, 25:84 (1989).

P. J. Houghton, et al., *Cancer Research*, 50:318 (1990).

P. J. Houghton, et al., *Cancer Research*, 50:664 (1990).

P. J. Houghton, et al., *Biochemical Pharmacology*, 39:1187 (1990).

P. H. Dhahir, et al., In *Proceedings of the 36th ASMS Conference on Mass Spectroscopy and Allied Topics*, pp. 972-973 (1988).

G. F. Holland, *Journal of Organic Chemistry*, 26:1662 (1961).

*Chemical Abstracts*, 52:17180; citing Haack, et al., East German Patent 9688, Apr. 21, 1955.

F. Kurzer, *Chemical Reviews*, 50:1 (1952).

G. B. Grindey, et al., In *Proceedings of the American Association for Cancer Research*, 28:309 (Abstract 1224) (1987).

H. Breuer, et al., *Chimie Therapeutique*, Nov./Dec. 1973:659.

L. J. Lerner, et al., *Metabolism*, 14:578 (1965).

*Primary Examiner*—Marianne M. Cintins
*Assistant Examiner*—Rebecca Cook
*Attorney, Agent, or Firm*—Paul J. Gaylo; Keroy Whitacker

[57] ABSTRACT

This invention provides the use of N-[[(3,4-dichlorophenyl)amino]carbonyl]-2,3-dihydrobenzofuran-5-sulfonamide, and pharmaceutically acceptable salts thereof, in the treatment of susceptible neoplasms in mammals. This invention further provides the novel aforementioned compound and its pharmaceutical formulations.

3 Claims, No Drawings

ANTITUMOR COMPOSITIONS AND METHODS

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to create new classes of compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best. B. E. Henderson, et al., Science, 254:1131–1137 (1991).

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics such as karyotype, morphology, iomnogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient.

This invention reports a sulfonylurea which is useful in the treatment of solid tumors. This compound is orally active—which, of course, results in less trauma to the patient—and is relatively non-toxic. This compound also has an excellent therapeutic index. The compound and its formulation are novel.

Many sulfonylureas are known in the art. Certain of these compounds are known to have hypoglycemic activities, and have been used medicinally as such agents. In addition, sulfonylureas have been taught to have herbicidal and antimycotic activities. General reviews of compounds of this structural type are taught by Kurzer, Chemical Reviews, 50:1 (1952) and C. R. Kahn and Y. Shechter, Goodman and Gilman's, The Pharmacological Basis of Therapeutics, (Gilman, et al., 8th ed. 1990) 1484–1487. Some diarylsulfonylureas have been reported as being active antitumor agents. e.g., U.S. Pat. No. 4,845,128 of Harper, (1989); European Patent Publication 0222475 (published May 20, 1987); European Patent Publication 0291269 (published Nov. 17, 1988); European Patent Publication 0467613 (published Jan. 22, 1992); Grindey, et al., American Association of Cancer Research, 27:277 (1986); and Houghton, et al., Cancer Chemotherapy and Pharmacology, 25:84–88 (1989).

Ongoing trials with the broad spectrum antineoplastic agent sulofenur [N-(indan-5-sulfonyl)-N'-(4-chlorophenyl)urea] have shown varying metabolic processes resulting in several major species and many minor species of metabolites. Initial preclinical pharmokinetic and disposition studies have been performed in mice, rats, dogs, and monkeys. These studies showed good adsorption and extensive metabolism of sulofenur in all species. The metabolic breakdown products of interest are as follows:

N-(1-hydroxyindan-5-sulfonyl)-N'-(4-chlorophenyl)urea;
N-(1-ketoindan-5-sulfonyl)-N'-(4-chlorophenyl)urea;
N-(3-hydroxyindan-5-sulfonyl)-N'-(4-chlorophenyl)urea;
N-(3-ketoindan-5-sulfonyl)-N'-(4-chlorophenyl)urea;
N-(1,2-dihydroxyindan-5-sulfonyl)-N'-(4-chlorophenyl)urea;
Dihydroxyindanyl metabolite;
p-Chloroaniline;
2-Amino-5-chlorophenyl sulfate;
p-Chloro-oxanilic acid;
W. J. Ehlhardt, Drug Metabolism and Disposition, 19:370–375 (1991).

The main urinary metabolites of sulofenur in animal trials were identified as the mono-hydroxy- and mono-ketoindanyl metabolites. The 1-hydroxy- and 1-ketoindansulfonylureas were also found to be the major metabolites in patients receiving the drug in phase I clinical studies. P. H. Dhahir, et al., Proceedings of the 6th ASMS Conference on Mass Spectroscopy and Allied Topics, pp. 972–973 (1988); W. J. Ehlhardt, supra at 372.

SUMMARY OF THE INVENTION

This invention provides a method of treating susceptible neoplasms in mammals which comprises administering to a mammal in need of said treatment an effective amount of a compound of the Formula I

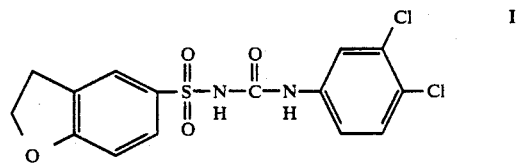

or a pharmaceutically acceptable salt thereof.

This invention also provides the novel compound of Formula I. Said compound is especially preferred in the treatment of susceptible neoplasms in mammals.

In addition, this invention provides pharmaceutical formulations comprising the compound of Formula I, in combination with a suitable pharmaceutical carrier, diluent, or excipient. These formulations are useful in the treatment of mammals suffering from susceptible neoplasms.

DETAILED DESCRIPTION OF THE INVENTION

The compound of Formula I is generally referred to as N-[[(3,4-dichlorophenyl)amino]carbonyl]-2,3-dihydrobenzofuran-5-sulfonamide. Alternatively the compound may be referred to as N-[5-(2,3-dihydrobenzofuryl)sulfonyl]-N'-(3,4-dichlorophenyl)urea or 1-(3,4-dichlorophenyl)-3-[5-(2,3-dihydrobenzofuran)sulfonyl]urea.

The compound of Formula I may be prepared by any number of methods known in the literature. These methods are generally summarized by Kurzer, Chemical Reviews, 50:1 (1952), especially pages 4–19. see also, R. W. Harper, et, al., European Patent Publication 291,269, published Nov. 17, 1988.

A preferred method of preparing the compound of Formula I is that of the reaction of a sulfonylisocyanate of Formula II

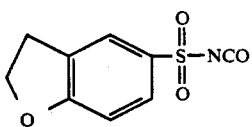

with the 3,4-dichloroaniline of Formula III

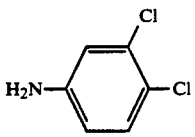

The reaction between compounds II and III is usually performed using equimolar amounts of the two reactants, although other ratios are operative. The reaction is best carried out in an aprotic non-reactive solvent such as benzene, toluene, acetonitrile, diethyl ether, tetrahydrofuran, dioxane, methylene chloride, or preferably acetone.

The reaction can be carried out at temperatures from about 0° C. up to about 100° C. At the preferred temperature range of about 20° C. to about 30° C., the reaction produces an exotherm and the reaction is usually complete within one hour. The product thus obtained is recovered by neutralization followed by filtration, and can be purified, if desired, by any number of methods known to those skilled in the art, such as chromatography or crystallization.

In another preferred method, the sulfonamide of Formula IV

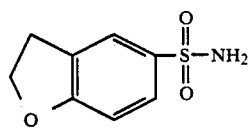

may be reacted with the isocyanate of Formula V

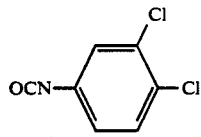

to provide the compound of Formula I. This reaction is generally conducted in a water miscible, non-reactive solvent such as tetrahydrofuran or acetone, in the presence of an acid scavenger such as sodium hydroxide, potassium hydroxide, lithium hydroxide, sodium methoxide, sodium hydride and the like. Generally, an equimolar amount or slight molar excess of the compound of Formula V is employed, although other ratios are operative.

The reaction may be performed at temperatures ranging from about 0° C. to about 100° C., although the preferred temperature range is from about 20° C. to about 30° C. At this preferred temperature the reaction is usually complete within about three hours.

Another method of preparing the compound of Formula I involves the reaction of the sulfonamide of Formula IV with an alkyl haloformate to provide carbamate VI which is then reacted with the substituted aniline of Formula III to provide the product of Formula I

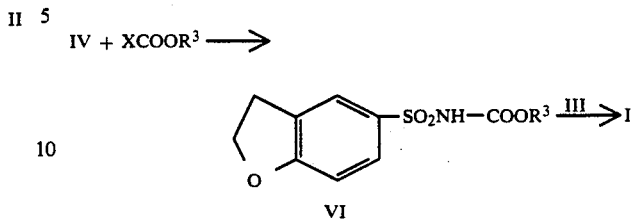

where X is bromo or chloro and $R^3$ is $C_1$–$C_3$ alkyl. The transformation of IV into VI is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative. This reaction is generally performed at a temperature from about 30° C. up to about 100° C. for a period of 1–6 hours to provide the desired intermediate of Formula VI. The intermediate of Formula VI and the substituted aniline of Formula III are then heated together in an inert high-boiling solvent, such as dioxane, toluene, or diglyme, at temperatures from about 50° C. up to the reflux temperature of the mixture to provide the desired product I.

The starting materials and intermediates for the preparation of the present compounds are commercially available or can be readily prepared by the above-described methods or other methods known in the literature.

This invention includes the pharmaceutically acceptable salts of the compound of Formula I. The compound of this invention can react with basic materials such as alkali metal- or alkaline earth metal hydroxides, carbonates, and bicarbonates including, without limitation, sodium hydroxide, sodium carbonate, potassium hydroxide, calcium hydroxide, lithium hydroxide, etc. to form pharmaceutically acceptable salts such as the corresponding sodium, potassium, lithium, or calcium salt. Nontoxic organic bases can also be used, including primary, secondary, and tertiary alkyl amines, such as methylamine, triethylamine, and the like.

The terms and abbreviations used in the instant example have their normal meanings unless otherwise designated. For example, "° C." refers to degrees Celsius; "N" refers to normal or normality; "mmole" means millimole; "g" refers to gram; "mL" means milliliter; "M" refers to molar or molarity; and "NMR" refers to nuclear magnetic resonance.

The following example further illustrates the preparation of the compound of Formula I. The example is illustrative only and is not intended to limit the scope of the invention in any way.

Preparation 2,3-Dihydrobenzofuran-5-sulfonamide

This compound was prepared essentially according to the teachings of J. A. Aikins, et al., European Patent Publication 254,577, published Jan. 27, 1988. N,N-dimethylformamide (23.0 mL, 297 mmol) was cooled in an ice-salt bath and treated dropwise with sulfuryl chloride (20.0 g, 148 mmol) at such a rate that the reaction temperature was maintained below 15° C. To this was added 2,3-dihydrobenzofuran (17.0 g, 142 mmol), and after warming to room temperature, the reaction mixture was rapidly heated to 130° C. over ten minutes, and then allowed to cool to room temperature. The reaction mixture was poured into water/ice/dichloromethane, 1/5/1 (700 mi), and the organic layer collected. The aqueous layer was diluted with water (100 mi) and extracted with dichloromethane. The combined organic phase was dripped into an ammonium hydroxide solution (3N, 250 mi), and allowed to stir overnight. Residual dichloromethane was removed by distillation and the resulting solid collected on a filter, washed with a small amount of water, followed by ether and then dried by aspiration to provide 12.8 g (45%) of the product.

Analysis of the product gave the following results: mp=163°-164.5° C.; $^1$H NMR (300 MHz, d$_6$-DMSO)$\delta$3.21 (t, 2H, J=8.8 Hz, CH$_2$), 4.60 (t, 2H, J=8.8 Hz, CH$_2$), 6.86 (d, 1H, J=8.4 Hz, Ar-H), 7.12 (bs, 2H, exchanges with D$_2$O, SO$_2$NH$_2$), 7.56 (d, 1H, J=8.4 Hz, Ar-H), 7.64 (s, 1H, Ar-H); IR(KBR) 3356, 3255, 1606, 1590, 1557, 1407, 1442, 1314, 1249, 1149, 1116, 1070, 982, 923 and 836 cm$^{-1}$; FDMS (MeOH) m/e 200 (M+).

Analysis for C$_8$H$_9$NO$_3$S:
Theory: C, 48.23; H, 4.55; N, 7.03; S, 16.09.
Found: C, 48.01; H, 4.71; N, 7.00; S, 16.36.

EXAMPLE

N-[5-(2,3-dihydrobenzofuryl)sulfonyl]-N'-(3,4-dichlorophenyl)urea

A solution of the product of Example 1 (29.6 g, 148.6 mmol) in acetone (75 mi) and 1N aqueous NaOH (150 mL, 150 mmol) was treated dropwise with a solution of 3,4-dichlorophenylisocyanate (30.0 g, 154.8 mmol) in 75 mL of acetone over 20 minutes. After stirring two hours, the insoluble bis(3,4-dichlorophenyl)urea was removed by filtration and the resulting clear solution neutralized by the addition of 1N aqueous HCl (150 mL, 150 mmol). The slurry was stirred 30 minutes, filtered and washed with water (500 mi), ether (200 mL), ether/hexane (1/1, 100 mL) and hexane (200 mL). Vacuum drying gave 50.1 g of crude product which was slurried in ethanol (300 mL) for one hour, collected on a filter and washed with ether. This ethanol reslurry was repeated and provided 42.7 g (74%) of the title compound after vacuum drying (50° C.).

Analysis of the product gave the following results: mp=188°-189° C.; $^1$H NMR (300 MHz, d$_6$-DMSO) $\delta$3.25 (t, 2H, J=8.8 Hz, CH$_2$), 4.63 (t, 2H, J=8.8 Hz, CH2), 6.92 (d, 1H, J=8.6 Hz, Ar-H), 7.25 (dd, 1H, J=2.5, 8.8 Hz, Ar-H), 7.48 (d, 1H, J=8.8 Hz, Ar-H), 7.68 (d, 1H, J=2.5 Hz, Ar-H), 7.71 (d, 1H, J=8.5 Hz, Ar-H), 7.77 (s, 1H, Ar-H), 9.08 (s, 1H, exchanges with D$_2$O, ArNH), 10.85, (bs, 1H, exchanges with D$_2$O, SO$_2$NH); IR(KBR) 3275, 1701, 1580, 1511, 1452, 1380, 12444, 1202, 1142, 1115, 1045, 896, 708 and 585 cm$^{-1}$; FDMS (MeOH) m/e 386, 388, 390 (M+).

Analysis for C$_{15}$H$_{12}$Cl$_2$N$_2$O$_4$S:
Theory: C, 46.53; H, 3.12; N, 7.23.
Found: C, 46.77; H, 3.24; N, 7.26.

The compound of Formula I has been shown to be active against transplanted human tumors in vivo. To demonstrate the anti-tumor activity of the compound of Formula I, the compound was tested in mice bearing different xenograft tumors.

Two of the tumor models used for showing the antineoplastic activity of the sulfonylurea of this invention were the human colon xenografts, HXGC3 and VRC5. J. A. Houghton and D. M. Taylor, *British Journal of Cancer*, 37:213-223 (1978). These tumors were obtained from St. Jude's Children's Research Hospital and have been widely used as human tumor models.

First passage tumors were stored in liquid nitrogen, using standard techniques. The transplanted tumor was reestablished from the Tumor Bank every six months or as needed. The tumor was maintained by serial passage twice weekly in nude mice.

In the procedures utilized here, the tumor was removed from passage animals and minced into 1- to 3-mm cubic fragments using sterile techniques. Tumor pieces were checked for sterility using both Antibiotic medium 1 and Brain Heart Infusion (Difco, Detroit, Mi.). The tumor pieces were implanted into the recipient CD1 Nu/Nu mice subcutaneously in an axillary site by trochar.

Drug therapy on the appropriate schedule was initiated seven days after tumor implantation. The compound being tested was mixed with 2.5% Emulphor EL620 from GAF Corporation (1:40 dilution in 0.9% saline). The total dosage volume for each administration was 0.5 mL. All animals were weighed at the beginning and end of administration of the subject compounds. Food and water were provided ad libitum.

Each control group and each dosage level of the treated groups consisted of 10 mice selected at random from the pool of implanted animals. The formulations were administered orally by gavage with the use of an 18-gauge needle. Compounds were dosed daily for 10 days.

The tumor was measured five days after treatment ended with two dimensional measurements (width and length) of the tumor taken using digital electronic calipers interfaced to a microcomputer. J. F. Worzalla, et al., *Investigational New Drugs*, 8:241-251 (1990). Tumor weights were calculated from these measurements using the following formula:

*Tumor weight (mg)=[tumor length (mm)×[tumor width (mm)]$^2$] ÷2*

At least one control group of an equal number of mice was treated with the same volume of 2.5% Emulphor only. The percent inhibition is determined by subtracting the ratio of the mean tumor size of the test group relative to the control group from one and multiplying the result by 100.

The results of several experiments in mice bearing the HXGC3 and VRC5 human colon adenocarcinomas when the instant compounds were administered orally are provided in Table I. In the Table, column 1 describes the particular human tumor xenograft being studied; column 2 gives the dosage level of the compound of Formula I in milligrams per kilogram of body weight; column 3 describes the percent inhibition of tumor growth; and column 4 tallies the number of mice which died during the course of the experiment relative to the total number of animals in the group.

TABLE 1

| Tumor | Dosage | Percent Inhibition | Toxic/Total |
|---|---|---|---|
| HXGC3 | 1200 | 99 | 0/10 |
| | 600 | 98 | 0/10 |
| | 300 | 98 | 0/10 |
| | 150 | 81 | 0/10 |
| VRC5 | 1200 | 100 | 0/10 |
| | 600 | 100 | 0/10 |

TABLE 1-continued

| Tumor | Dosage | Percent Inhibition | Toxic/Total |
|-------|--------|--------------------|-------------|
|       | 300    | 98                 | 0/10        |
|       | 150    | 97                 | 0/10        |

As a result of the high therapeutic index of the compound of Formula I, toxicological studies were performed to determine whether the compound of the current invention possessed the same adverse reaction profile of sulofenur. For these experiments thirty male Fischer 344 rats were administered varying dosages of a formulation containing the compound of Formula I. These formulations contained between 65 and 1000 mg of the active ingredient per kilogram of body weight of the rat, in combination with a suitable excipient, usually containing 10% acacia. The compounds were administered orally by gavage. The compounds were dosed daily for 14 days. All animals were weighed at the beginning and end of administration of the subject compounds. Food and water were provided ad libitum.

Upon completion of the testing regimen, morphological and hematological studies were performed. These studies indicated an absence of hemolytic anemia, which is the dose-limiting toxicity of sulofenur. Pathological studies performed indicate effectiveness against tissues with a high mitotic index, including lymph nodes, thymus, gut, testis, and bone marrow, these changes being consistent with the tissue effects produced by other efficacious anticancer drugs. Unexpected tissue changes were not observed, demonstrating a more limited adverse reaction profile than other compounds of its class.

The compound of Formula I is an antineoplastic agent and the invention provides a method of treating susceptible neoplasms. In particular, the present compound is useful in treating solid tumors including carcinomas such as ovarian, non-small cell lung, gastric, pancreatic, prostate, renal cell, breast, colorectal, small cell lung, melanoma, and head and neck; and sarcomas such as Kaposi's sarcoma and rhabdomyosarcoma.

The instant compound is usually administered in the form of a pharmaceutical composition, preferably orally. Such compositions are prepared in a manner well known in the pharmaceutical art and comprise at least one active compound. Accordingly, the present invention also includes pharmaceutical compositions which contain, as the active ingredient, the compound of Formula I associated with a pharmaceutically acceptable carrier. The invention further comprises the method of treating susceptible neoplasms using compositions containing as an active ingredient the compound of Formula I.

In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 1200 mg/kg of body weight. In the treatment of adult humans, the range of about 1 to about 50 mg/kg, in single or divided dose, is preferred. However, it will be understood that the amount of the compound actually administered will be determined by a physician, in the light of the relevant circumstances, including the condition to be treated, the chosen route of administration, the age, weight, and response of the individual patient, and the severity of the patient's symptoms, and therefore the above dosage ranges are not intended to limit the scope of the invention in any way.

Formulation 1

Hard gelatin capsules are prepared using the following ingredients:

| | |
|---|---|
| N-[[(3,4-dichlorophenyl)amino]carbonyl]-2,3-dihydrobenzofuran-5-sulfonamide | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the ingredients below:

| | Quantity (mg/tablet) |
|---|---|
| N-[[(3,4-dichlorophenyl)amino]carbonyl]-2,3-dihydrobenzofuran-5-sulfonamide | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

| | Weight % |
|---|---|
| N-[[(3,4-dichlorophenyl)amino]carbonyl]-2,3-dihydrobenzofuran-5-sulfonamide | 5 |
| Lactose | 95 |

The active mixture is mixed with the lactose and the mixture is added to a dry powder inhaling appliance.

Formulation 4

Tablets, each containing 60 mg of active ingredient, are prepared as follows:

| N-[[(3,4-dichlorophenyl)amino]carbonyl]-2,3-dihydrobenzofuran-5-sulfonamide | 60.0 mg |
|---|---|
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–600° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of medicament are made as follows:

| N-[[(3,4-dichlorophenyl)amino]carbonyl]-2,3-dihydrobenzofuran-5-sulfonamide | 80.0 mg |
|---|---|
| Starch | 109.0 mg |
| Magnesium stearate | 1.0 mg |
| Total | 190.0 mg |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient are made as follows:

| N-[[(3,4-dichlorophenyl)amino]carbonyl]-2,3-dihydrobenzofuran-5-sulfonamide | 225 mg |
|---|---|
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of medicament per 5.0 mL dose are made as follows:

| N-[[(3,4-dichlorophenyl)amino]carbonyl]-2,3-dihydrobenzofuran-5-sulfonamide | 50.0 mg |
|---|---|
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor | q.v. |
| Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of medicament, are made as follows:

| N-[[(3,4-dichlorophenyl)amino]carbonyl]-2,3-dihydrobenzofuran-5-sulfonamide | 150.0 mg |
|---|---|
| Starch | 407.0 mg |
| Magnesium stearate | 3.0 mg |
| Total | 560.0 mg |

The active ingredient, cellulose, starch, and magnesium stearate are blended, passed through a No. 20 mesh U.S. sieve, and filled into hard gelatin capsules in 560 mg quantities.

We claim:

1. A method of treating susceptible neoplasms in mammals which comprises administering to a mammal in need of said treatment an effective amount for treating susceptible neoplasms of a compound of the formula

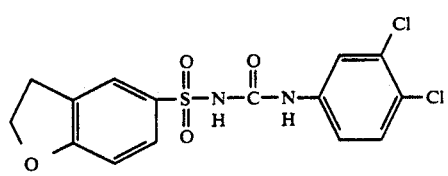

or a pharmaceutically acceptable salt thereof.
2. A compound of the formula
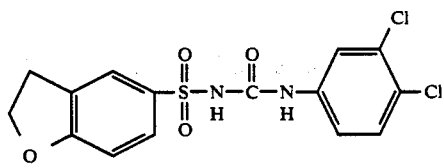
and pharmaceutically acceptable salts thereof.
3. A pharmaceutical formulation comprising an effective amount of a compound of the formula
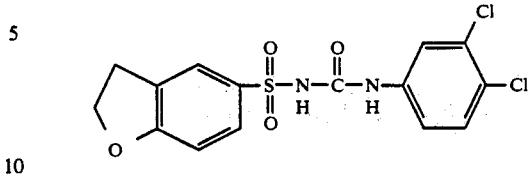
or a pharmaceutically acceptable salt thereof, in combination with a suitable pharmaceutical excipient.
* * * * *